United States Patent
Langley et al.

(10) Patent No.: US 10,144,686 B2
(45) Date of Patent: *Dec. 4, 2018

(54) SYSTEM AND METHOD TO REMOVE ORGANIC ACID FROM A RICH MEG STREAM BY STRIPPING

(71) Applicant: Cameron Solutions, Inc., Houston, TX (US)

(72) Inventors: Steven Langley, Croydon (GB); David John Knight, Kuala Lumpur (MY)

(73) Assignee: Cameron Solutions, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/675,260

(22) Filed: Aug. 11, 2017

(65) Prior Publication Data

US 2018/0029963 A1 Feb. 1, 2018

Related U.S. Application Data

(63) Continuation of application No. 15/089,076, filed on Apr. 1, 2016, now Pat. No. 9,732,019.

(51) Int. Cl.
| | | |
|---|---|---|
| *C07C 29/76* | (2006.01) | |
| *B01D 3/00* | (2006.01) | |
| *B01D 53/00* | (2006.01) | |
| *B01D 53/78* | (2006.01) | |
| *C10L 3/10* | (2006.01) | |
| *B01D 3/34* | (2006.01) | |
| *C07C 51/41* | (2006.01) | |
| *B01D 3/14* | (2006.01) | |
| *C07C 29/80* | (2006.01) | |
| *B01D 53/72* | (2006.01) | |

(52) U.S. Cl.
CPC ............ *C07C 29/76* (2013.01); *B01D 3/00* (2013.01); *B01D 3/143* (2013.01); *B01D 3/343* (2013.01); *B01D 53/72* (2013.01); *B01D 53/78* (2013.01); *C07C 29/80* (2013.01); *C07C 51/412* (2013.01); *C10L 3/107* (2013.01)

(58) Field of Classification Search
CPC .......... C07C 29/76; B01D 3/343; B01D 53/78
See application file for complete search history.

(56) References Cited

U.S. PATENT DOCUMENTS

| | | |
|---|---|---|
| 4,898,644 A | 2/1990 | Van Horn |
| 2015/0104356 A1 | 4/2015 | Messenger |
| 2015/0119609 A1 | 4/2015 | Deshmukh |

FOREIGN PATENT DOCUMENTS

EP 2860168 4/2015

*Primary Examiner* — Sikarl A Witherspoon
(74) *Attorney, Agent, or Firm* — Gable Gotwals

(57) ABSTRACT

A system and method for removing acetic acid and other short chain fatty acids described as organic acid from a rich mono-ethylene glycol ("MEG") solution does so by stripping the organic acid from the rich MEG solution by contacting the solution with a gas, the gas being nitrogen or a fuel gas such as methane; and stripping the organic acid from the gas by contacting the gas with a caustic solution such as a dilute sodium hydroxide solution. The stripping steps take place in respective stripping columns. A portion of the gas exiting the gas/organic acid stripping column can be recycled to the MEG/organic acid stripping column to reduce total gas usage. A portion of the waste stream exiting the gas/organic acid stripping column can be recycled back to the gas/organic acid stripping column to reduce the amount of caustic solution used as well as the amount of waste.

20 Claims, 2 Drawing Sheets

FIG. 2

| Names | Units | Rich MEG with Acetic | Rich MEG | Gas make-up | Gas/acetic | Gas purge | Gas recycle | Caustic Solution | Waste Water / Acetic |
|---|---|---|---|---|---|---|---|---|---|
| Temperature | °C | 60.0 | 59.0 | 40.0 | 60.0 | 41.5 | 41.5 | 40.2 | 41.9 |
| Pressure | bar | 2.0 | 2.1 | 3.9 | 2.0 | 2.1 | 2.1 | 5.5 | 5.5 |
| Mass Flow | kg/h | 52213 | 52068 | 100 | 1245.6 | 108.0 | 1000 | 5000 | 5137.6 |
| Volumetric Flow | m³/h | 50.85 | 50.68 | 40.79 | 967.31 | 79.12 | 732.49 | 5.00 | 5.13 |
| Mass Density | kg/m³ | 1026.8 | 1027.4 | 2.45 | 1.29 | 1.37 | 1.37 | 1000.7 | 1001.9 |
| Water(Mass Fraction) | % | 59.90 | 59.90 | - | 8.53 | 4.04 | 4.04 | 99.00 | 97.5 |
| MEG(Mass Fraction) | % | 39.90 | 40.00 | - | 0.06 | 23.6 ppbW | 23.6 ppbW | - | 135 ppmW |
| NaOH(Mass Fraction) | % | 0.00 | 0.00 | - | 0.00 | 0.00 | 0.00 | 1.00 | 0.973 |
| Acetic Acid(Mass Fraction) | ppm | 1497 | 94.77 | - | 58310 | 0.01823 | 0.01823 | - | 14260 |
| Propionic Acid(Mass Fraction) | ppm | 89.85 | 38.22 | - | 19990 | 22190 | 22190 | - | 59.1 |
| Formic Acid(Mass Fraction) | ppm | 29.95 | 0.06561 | - | 1253 | 0.0001793 | 0.0001793 | - | 303.7 |
| Butyric Acid(Mass Fraction) | ppm | 69.89 | 19.63 | - | 20480 | 22890 | 22890 | - | 30.2 |

SYSTEM AND METHOD TO REMOVE ORGANIC ACID FROM A RICH MEG STREAM BY STRIPPING

CROSS-REFERENCE TO RELATED APPLICATIONS

This application is a continuation application of U.S. patent application Ser. No. 15/089,076, filed Apr. 1, 2016, now U.S. Pat. No. 9,732,019, the contents of which are hereby incorporated by reference in its entirety.

BACKGROUND

This invention relates to processes designed to treat mono ethylene glycol ("MEG") used in the oil and gas industry to control hydrates formation. More particularly, the invention relates to MEG reclamation processes which are designed to remove salts from a wet MEG feed stream.

In the oil and gas industry, dry (lean) MEG is used to control the formation of hydrates within a produced stream. Once used, the now wet (rich) MEG is, in turn, dried and cleaned by way of a MEG regeneration and reclamation process so the MEG can be used again in hydrate control. The systems and methods used to recover MEG usually include three sections: pre-treatment, flash separation, and MEG regeneration. These sections can be followed by salt management and followed or preceded by a calcium removal section.

The MEG used for hydrate inhibition in natural gas pipelines has a similar volatility to organic acids such as acetic acid. Therefore, if water from a well contains organic acids, the organic acid tends to stay with the MEG solution. Removing this organic acid can require large, costly and wasteful blowdown or purges of MEG.

Other options for the removal of organic acid from rich MEG include boiling off the organic acids, distillation of the rich MEG and organic acid, and precipitation using divalent cations. The boiling off method requires a relatively large heating duty to heat the whole stream and/or vacuum conditions. Because the relative volatilities of MEG and organic acid are similar this method also produces large MEG losses. The distillation method, similar to the boiling off method, requires a large heating (reboiling) and cooling (condensing) duty. Although the MEG losses are reduced by distillation, more equipment is required (e.g., column, reboiler, condenser). The precipitation method requires the addition of chemicals to increase the pH and a solid separation step such as centrifuge or filtration (see e.g. US 2015/0119609 A1).

SUMMARY

A preferred embodiment of a system and method for removing acetic acid and other short chain fatty acids described as organic acids from a rich mono-ethylene glycol ("MEG") solution does so by:
  adjusting, if needed, the pH of the rich MEG solution to a pH<4 to ensure the organic acids are in acid form;
  stripping the organic acids from the rich MEG solution by contacting the solution with a gas, the gas being nitrogen or a fuel gas such as methane; and
  washing organic acids from the gas by contacting the gas with a caustic solution such as a dilute sodium hydroxide solution.

The stripping/washing steps take place in respective stripping columns. A portion of the gas exiting the gas/organic acid washing column can be recycled to the MEG/organic acid stripping column to reduce total gas usage. A portion of the waste stream exiting the gas/organic acid washing column can be recycled back to the gas/organic acid washing column to reduce the amount of caustic solution used as well as the amount of waste.

This method can be used as part of a MEG regeneration and reclamation process to remove acetic acid and other short chain fatty acids described as organic acids from rich MEG. The method reduces the amount of blowdown required, reduces the overall MEG loss, and does not require boiling off, distillation or precipitation steps.

Unlike the boiling off method, this method requires no heat input, no vacuum conditions, and has relatively low MEG losses. Unlike the distillation method, this method requires a low energy input, no heat input, much less cooling duty, operates at a much lower and therefore safer temperature, and does not require additional large equipment items like a reboiler or condenser. Unlike the precipitation method, this method operates at a low pH (as normally seen in rich MEG) so pH adjustment is minimized and does not require a solid separation step which can be expensive, complicated and have a low reliability.

BRIEF DESCRIPTION OF THE DRAWINGS

FIG. 2 is a table showing the results of a simulation of the method of FIG. 1 using PROMAX® software.

ELEMENTS USED IN THE DRAWINGS AND DETAILED DESCRIPTION

Figure 1:
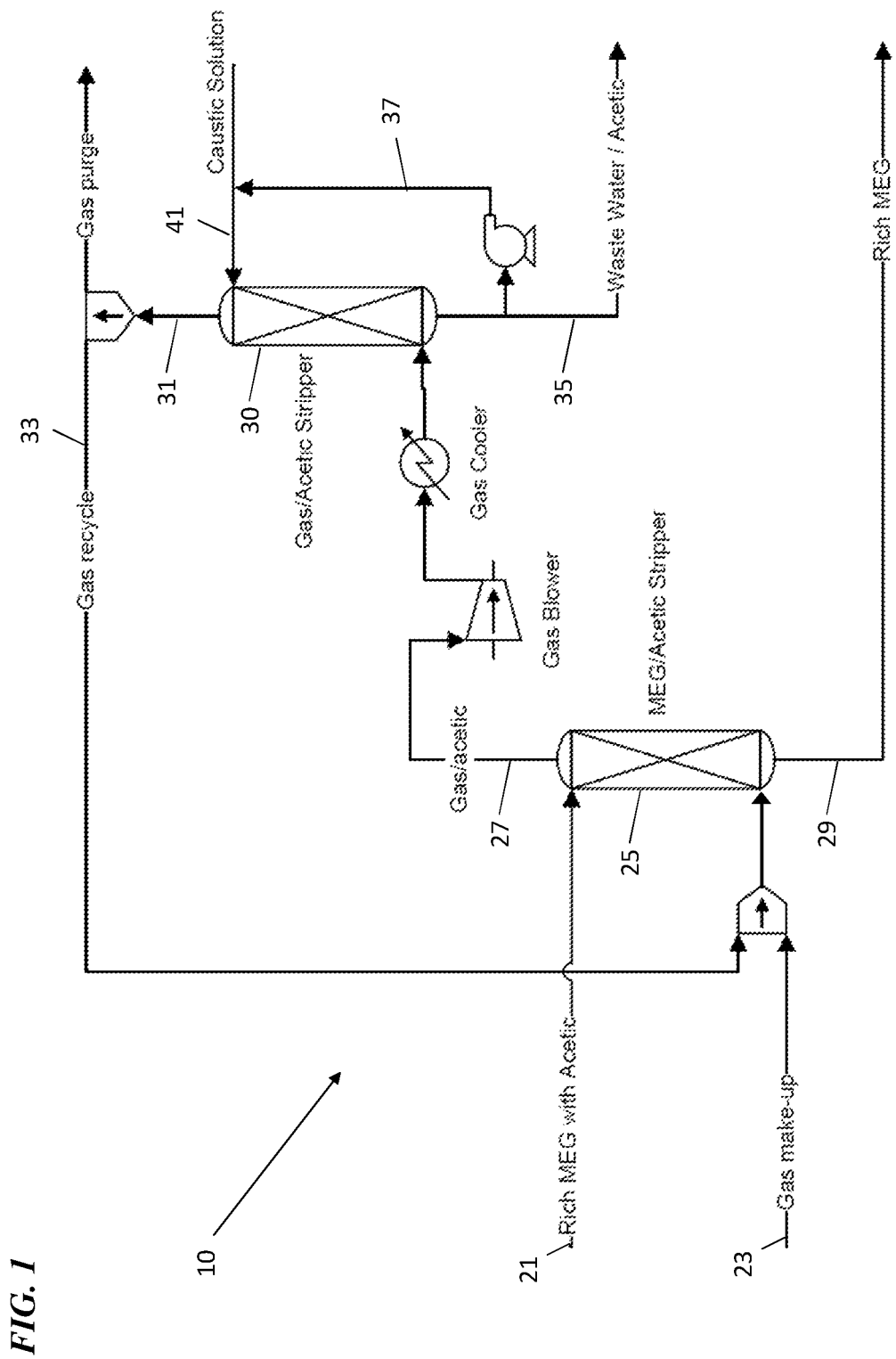
FIG. 1 is a preferred embodiment of the method.

10 System or method
21 Rich MEG solution or stream containing organic acid
23 Gas make-up stream
25 MEG/organic acid stripper column
27 Gas stream containing the organic acid stripped from the 21)
29 Rich MEG stream without or substantially free of the organic acid
30 Gas/organic acid stripper column
31 Gas stream without or substantially free of the organic acid
33 Gas recycle stream portion of 31
35 Waste water stream
41 Solution

DETAILED DESCRIPTION OF THE PREFERRED EMBODIMENTS

For the purpose of this disclosure, an "organic acid" is a carboxylic acid having a general formula R—C(O)OH, where R is H (formic acid), $CH_3$ (acetic acid), $CH_3CH_2$ (propionic acid), or $CH_3(CH_2)_2$ (butyric acid)) and where the total number of carbon atoms C is no greater than 4.

Referring to FIG. 1, a wet or rich MEG stream 21 containing an organic acid is routed to a MEG/organic acid stripper column 25 where the rich MEG stream 21 is contacted by a gas make-up stream 23 or gas recycle stream 33 (or some combination of the streams 23, 33). Gas 23, 33 can be a fuel gas such as natural gas or can be nitrogen. The pH of the rich MEG stream 21 can be monitored and adjusted when needed to a pH<4. This helps ensure the organic acid is in acid form.

The gas 23, 33 that has stripped the organic acid from the stream 21 exits a top end of the MEG/organic acid stripper column 25 as a gas stream 27 containing the organic acid. A rich MEG stream 29 without organic acid (or substantially free of organic acid) exits a bottom end of the column 25. "Substantially free of organic acid" means at least 90% of the acetic acid present in the rich MEG stream 21 is removed. If other organic acids are present in stream 21, preferably at least 50% of those organic acids are also stripped from the rich MEG stream 21.

The gas stream 27 containing the organic acids stripped from stream 21 is routed to a gas/organic acid washing column 30 where the stream 27 is contacted by the solution 41. Solution 41 can be a dilute sodium hydroxide solution (e.g., 1.0 wt % NaOH and water) or its equivalent. A gas stream 31 without organic acid (or substantially free of organic acid) exits at the top end of the column 30. "Substantially free of organic acid" means at least 90% of the acetic acid is washing from the gas stream 27 containing organic acids. Preferably at least 95% is removed.

A waste water stream 35 containing organic acid exits the bottom end of the gas stripper column 25. This stream 35 can be recycled to the gas/organic acid washing column 30. The gas steam 31 can be recycled to the MEG/organic acid stripper column 25 as a recycle gas stream 33.

Preferably, the temperature range operated in is about 40° C. to 60° C., with 60° C. for the rich MEG stream 21 and gas stream 27 containing organic acids, 40° C. for the gas make-up and recycle streams 23, 33, and 40° for solution 41 and water streams. Those temperatures can vary depending on the application-specific requirements.

Referring to FIG. 2, and by way of example only, a simulation using a rich MEG stream of 50.85 m$^3$/hr containing 1497 ppm acetic acid shows that 94% of the acetic acid can be stripped from the rich MEG stream by circulating 1100 kg/hr of stripping gas in the MEG/organic acid stripping column, where 100 kg/hr is provided by the gas make-up flow and 1000 kg/hr is provided by the recycled gas flow. The method also removes 57% of the incoming propionic acid, 99% of the formic acid, and 72% of the butyric acid.

The use of a caustic solution such as a dilute sodium hydroxide solution in the gas/organic acid washing removes >99% of the acetic acid from the stripping gas. About 90% of the now substantially organic acid-free stripping gas is then recycled in the MEG/organic acid stripper column. This minimizes the amount of stripping gas make-up. A portion of the caustic solution can also be recycled to minimize the amount of caustic and water make-up as well as reduce the waste stream exiting the gas/organic acid washing column.

The preferred embodiments described above and illustrated in the drawing figures provide examples of the system and method. The following claims define the inventive system and method and cover the full range of equivalents to which the recited elements of the claims are entitled.

What is claimed:

1. A method for removing organic acid from a MEG stream, the method comprising:
   stripping the organic acid from the MEG stream after a hydrate inhibition use of the MEG stream by contacting the MEG stream with a gas
   wherein the MEG stream after the contact with the gas is substantially free of the organic acid.

2. A method according to claim 1 further comprising:
   washing the organic acid contained in the gas that contacted the MEG stream by contacting the gas with a caustic solution
   wherein the gas after the contact with the caustic solution is substantially free of the organic acid.

3. A method according to claim 2 further comprising recycling a portion of the gas for use in the stripping of the organic acid from the MEG stream.

4. A method according to claim 2 further comprising recycling a portion of a waste stream from the washing of the organic acid contained in the gas for use in the washing of the organic acid contained in the gas.

5. A method according to claim 2 wherein the caustic solution is a sodium hydroxide solution comprising about 1% sodium hydroxide.

6. A method according to claim 1 further comprising adjusting, when needed, a pH of the MEG stream to a pH<4.

7. A method for removing organic acid from a MEG stream, the method comprising the steps of:
   stripping the organic acid from the MEG stream after a hydrate inhibition use of the MEG stream by contacting the MEG stream with a gas wherein the MEG stream after the contact with the gas is substantially free of the organic acid; and
   washing the organic acid contained in the gas that contacted the MEG stream by contacting the gas with a caustic solution, wherein the gas after contact by the caustic solution is substantially free of the organic acid.

8. A method according to claim 7 wherein the organic acid is a carboxylic acid.

9. A method according to claim 7 further comprising recycling a portion of the gas for use in the stripping of the organic acid from the MEG stream.

10. A method according to claim 7 further comprising recycling a portion of a waste stream from the washing of the organic acid contained in the gas for use in the washing of the organic acid contained in the gas.

11. A method according to claim 7 wherein the caustic solution is a sodium hydroxide solution comprising about 1% sodium hydroxide.

12. A method according to claim 7 further comprising the step of adjusting, when needed, a pH of the MEG stream to a pH<4.

13. A MEG reclamation and regeneration system the system comprising
   a MEG/organic acid stripping column; and
   a gas/organic acid washing column;
   the MEG/organic acid stripping column configured to receive a stripping gas and a MEG stream containing the organic acid, the MEG stream exiting the MEG/organic stripping column as a substantially organic acid-free rich MEG stream; the stripping gas including the organic acid exiting the MEG/organic stripping column; and
   the gas/organic acid washing column configured to receive a caustic solution and the stripping gas including the organic acid exiting the MEG/organic stripping column, the gas exiting the gas/organic washing column as a substantially organic acid free gas stream.

14. A system according to claim 13 further comprising a recycle loop, the recycle loop configured to receive a portion of the substantially organic acid gas free stream exiting the gas/organic acid washing column and route the portion back to the MEG/organic stripping column.

15. A system according to claim 13 further comprising a recycle loop, the recycle loop configured to receive a portion of a waste stream exiting the gas/organic acid washing column and route the portion back to the gas/organic acid washing column.

16. A system according to claim 13, the stripping gas being nitrogen.

17. A system according to claim 13, the stripping gas being methane.

18. A MEG regeneration and reclamation system comprising:
- a MEG/organic acid stripping column; and
- a gas/organic acid washing column;
  - the MEG/organic acid stripping column configured to receive a stripping gas and a MEG stream containing an organic acid;
    - the MEG stream exiting the MEG/organic stripping column as a substantially organic acid-free MEG stream;
  - the gas/organic acid washing column arranged to receive a caustic solution and the stripping gas containing the organic acid exiting the MEG/organic stripping column,
    - the stripping gas exiting the gas/organic washing column as a substantially organic acid-free gas stream;
  - wherein a pH of the MEG stream is less than 4; and
  - wherein the stripping gas is selected from the group consisting of nitrogen and methane.

19. A system according to claim 18, the stripping gas being selected from a group consisting of nitrogen and methane.

20. A system according to claim 18 further comprising a first and a second recycle loop,
- the first recycle loop configured to receive a portion of the substantially organic acid gas free stream exiting the gas/organic acid washing column and route the portion back to the MEG/organic stripping column;
- the second recycle loop configured to receive a portion of a waste stream exiting the gas/organic acid washing column and route the portion back to the gas/organic acid washing column.

* * * * *